(12) United States Patent
Hwang et al.

(10) Patent No.: US 6,740,034 B2
(45) Date of Patent: May 25, 2004

(54) THREE-DIMENSIONAL ULTRASOUND IMAGING SYSTEM FOR PERFORMING RECEIVE-FOCUSING AT VOXELS CORRESPONDING TO DISPLAY PIXELS

(75) Inventors: Jae Sub Hwang, Seoul (KR); Tai Kyong Song, Seoul (KR)

(73) Assignee: Medison Co., LTD, Kangwon-do (KR)

( * ) Notice: Subject to any disclaimer, the term of this patent is extended or adjusted under 35 U.S.C. 154(b) by 0 days.

(21) Appl. No.: 10/133,159

(22) Filed: Apr. 26, 2002

(65) Prior Publication Data

US 2002/0193688 A1 Dec. 19, 2002

(30) Foreign Application Priority Data

Apr. 27, 2001 (KR) ........................................ 2001-22831

(51) Int. Cl.[7] ................................................. A61B 8/00
(52) U.S. Cl. ....................... 600/437; 600/443; 600/447; 128/916
(58) Field of Search ................................. 600/437–472; 128/916; 342/185.81; 345/424, 643

(56) References Cited

U.S. PATENT DOCUMENTS

| | | | | |
|---|---|---|---|---|
| 5,197,037 A | * | 3/1993 | Leavitt | 367/11 |
| 5,390,674 A | * | 2/1995 | Robinson et al. | 600/443 |
| 5,497,776 A | * | 3/1996 | Yamazaki et al. | 600/445 |
| 5,531,224 A | * | 7/1996 | Ellis et al. | 600/437 |
| 5,609,485 A | * | 3/1997 | Bergman et al. | 434/262 |
| 5,766,129 A | * | 6/1998 | Mochizuki | 600/443 |
| 5,787,889 A | * | 8/1998 | Edwards et al. | 600/443 |
| 5,957,138 A | * | 9/1999 | Lin et al. | 600/453 |
| 6,048,312 A | * | 4/2000 | Ishrak et al. | 600/443 |
| 6,155,978 A | * | 12/2000 | Cline et al. | 600/443 |
| 6,248,073 B1 | * | 6/2001 | Gilbert et al. | 600/447 |
| 6,280,387 B1 | * | 8/2001 | Deforge et al. | 600/454 |

* cited by examiner

Primary Examiner—Dennis W. Ruhl
Assistant Examiner—William C. Jung
(74) Attorney, Agent, or Firm—Thelen Reid & Priest LLP; David B. Ritchie

(57) ABSTRACT

A three-dimensional (3D) ultrasound imaging system performs receive-focusing at voxels corresponding to pixels of a display device. The system comprises a display device; transducers for transmitting ultrasound signals toward the object and receiving echo signals from a voxel corresponding to a pixel on the display device, wherein the voxel is on a scanning region of the object; an RF volume memory for storing signals from the transducers; a signal processor for processing the stored signals to obtain 3D data sets with respect to the voxel; and an image former for forming the 3D image.

6 Claims, 7 Drawing Sheets

THREE-DIMENSIONAL ULTRASOUND IMAGING SYSTEM FOR PERFORMING RECEIVE-FOCUSING AT VOXELS CORRESPONDING TO DISPLAY PIXELS

FIELD OF THE INVENTION

The present invention relates to an ultrasound imaging system, and more particularly, to a three-dimensional ultrasound imaging system for performing receive-focusing at voxels corresponding to pixels of a display device.

BACKGROUND OF THE INVENTION

Ultrasound imaging systems are widely used in the medical diagnostic field for their ability to obtain the image of an object non-invasively, i.e., by transmitting ultrasound signals to the object and processing their reflection. conventional, three-dimensional (3D) ultrasound imaging systems have an array of ultrasound transducers or probes for generating ultrasound pulses and receiving echo signals of the ultrasound pulses reflected off an object. Ultrasound pulses from the array of ultrasound transducers are transmit-focused to a desired point by controlling the timing of the ultrasound pulse generation at each of the transducers. Specifically, the timing control of the ultrasound pulse generation compensates for propagation delays due to the different distances between respective transducers and particular points on a scan line. By sequentially delaying the generation of ultrasound pulses from the transducers, all the ultrasound pulses are simultaneously focused to a particular point. Simultaneous reception of the reflected ultrasound pulses by the array of transducers is also made possible by sequentially adjusting the receive-timings of respective transducers—the greater the distance from a respective transducer to a particular point, the more receive delay provided to that transducer.

In order to obtain an accurate 3D image of an object, transmit-focusing to multiple points on the target object is needed. But after the transmission of ultrasound pulses to the target point, transmission to another target point must wait until all the reflected ultrasound pulses are received, including the one reflected from the farthest point. Increasing the number of transmit focal points has the drawback of increasing the amount of time required to obtain an 3D image, thus reducing the frame rate.

Where the transmission focuses on a single point, the frame rate is determined by the following equation:

$$\frac{1}{FR} = \frac{2D}{c} \times N \qquad \text{Eq. (1)}.$$

FR is the frame rate; D is the depth of the scan; c is the velocity of ultrasound transmission in the medium; and N is the number of scan lines. As seen in Eq. 1, the frame rate is inversely proportional to the number of scan lines. Thus, there is a trade-off between frame rate and the number of scan lines.

One conventional solution is the sequential application of a radial scan pattern over the entire diagnostic area along N number of the scan lines to predetermined points. In addition to a radial scan pattern, a parallel scan line pattern has also been widely used. With these scanning methods, i.e., dynamic receive-focusing methods, the receive-focusing is achieved only on points along the scan lines, limiting collection of data of an object to these points of the scan lines.

Referring to FIG. 1, 3D ultrasound imaging system 100 includes transducer array 102, beamformer 104, envelope detector 106, log compensator 108, digital scan converter 110, image former 112, and display device 114. Envelope detector 106 and log compensator 108 constitute echo signal processing unit 116. Array 102 sequentially transmits ultrasound pulses to be focused on target points on the scan lines of an object. After transmitting the ultrasound pulses to one of the scan lines, the respective transducers receive echoes reflected from the target points. Beamformer 104 focuses the received echo from a target point on the scan lines for storage in the form of radio frequency (RF) data. Beamformer 104 repeats this receive-focusing for each of the target points on every scan line, to acquire data about the shape of the object. The data acquired by beamformer 104 is processed through envelope detector 106, log compensator 108, and digital scan converter 110, to thereby become a 3D data set used in obtaining desired 3D images.

Display device 114 generally has pixels arranged in a matrix on its screen and each pixel should be provided with display data to form a 3D image. Digital scan converter 110 first stores data which is receive-focused and the converts the data to a horizontal raster line display format used in most display devices. The converted data is the 3D data set. The 3D data set of the object, acquired by using the dynamic receive-focusing scheme, is limited to the focused target points on the scan lines. These focused target points do not necessarily coincide with actual pixel points on the display device (these actual pixel points corresponding to the pixel locations on the display device will simply be referred to as "pixel points" hereafter). Thus, digital scan converter 110 has to perform 3D (R–θ) interpolation, as is well known in the art, on the 3D data set to provide display data for all the pixels of the display device. For example, in the case of a radial scan pattern, because the distance between adjacent scan lines become greater as you get farther away from the transducers, the number of pixel points is greater where a 3D data set is not acquired directly from the receive-focused data. Using the 3D data set from digital scan converter 110, image former 112 forms a 3D image to display on display device 114. Digital scan converter 110 must also perform interpolation in the case of a parallel scan pattern.

Thus, conventional 3D ultrasound imaging systems first obtain a 3D data set after forming a 2D image, by using display data acquired in one frame, and then form a 3D image based on that 3D data set. Consequently, the quality of the 3D image is dependent on the 2D image. Because conventional systems must perform this digital scan conversion to obtain 3D data sets, some distortion is introduced into the 3D image.

SUMMARY OF THE INVENTION

It is, therefore, an object of the present invention to provide a three-dimensional (3D) ultrasound imaging system for forming a 3D image comprising: a display device; at least one transducer, for transmitting ultrasound signals toward an object and receiving echo signals from a voxel corresponding to a pixel on the display device, wherein the voxel is on a scanning region of the object; signal storing means for storing signals from at least one of the transducers; signal processing means for processing the stored signals to obtain 3D data sets with respect to the voxel; and image forming means for forming a 3D image based on the 3D data sets.

BRIEF DESCRIPTIONS OF THE DRAWINGS

The above and other objects and features of the present invention will become apparent from the following description of preferred embodiments given in conjunction with the accompanying drawings.

DETAILED DESCRIPTION OF THE PRESENT INVENTION

A three-dimensional (3D) ultrasound imaging system in accordance with the present invention will be described with reference to FIGS. 2 and 7.

Figure 2:
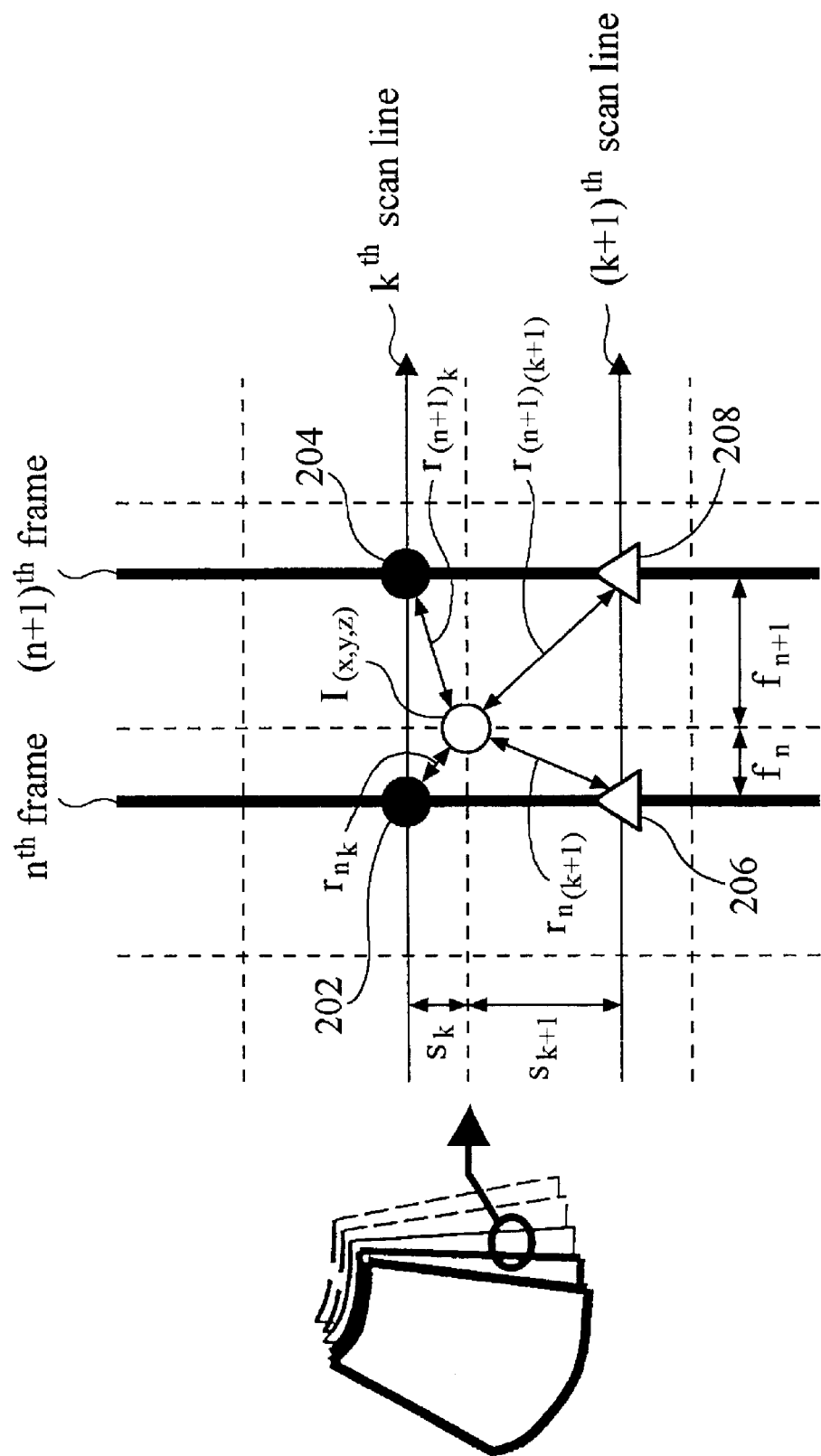
FIG. 2 is a two-dimensional (2D) representation of a voxel corresponding to one of the pixels on a display device and the RF data surrounding the voxel in accordance with the present invention.

Referring first to FIG. 2, there is a two-dimensional (2D) representation of a voxel corresponding to a pixel on a display device and RF data 202–208 surrounding the voxel, wherein the voxel exists on a space between consecutive frames. For the sake of convenience, voxel I(x, y, z) is represented on a 2D plane by projecting spatial positions of scan lines of each frame and voxel I(x, y, z) at the apex of the adjacent frames spatially closest to voxel I(x, y, z) corresponding to the pixel on the display device. Unlike conventional methods, the receive-focusing method in accordance with the present invention receive-focuses echo signals from voxel I(x, y, z) to directly obtain 3D data sets necessary for forming a 3D image.

Figure 3:
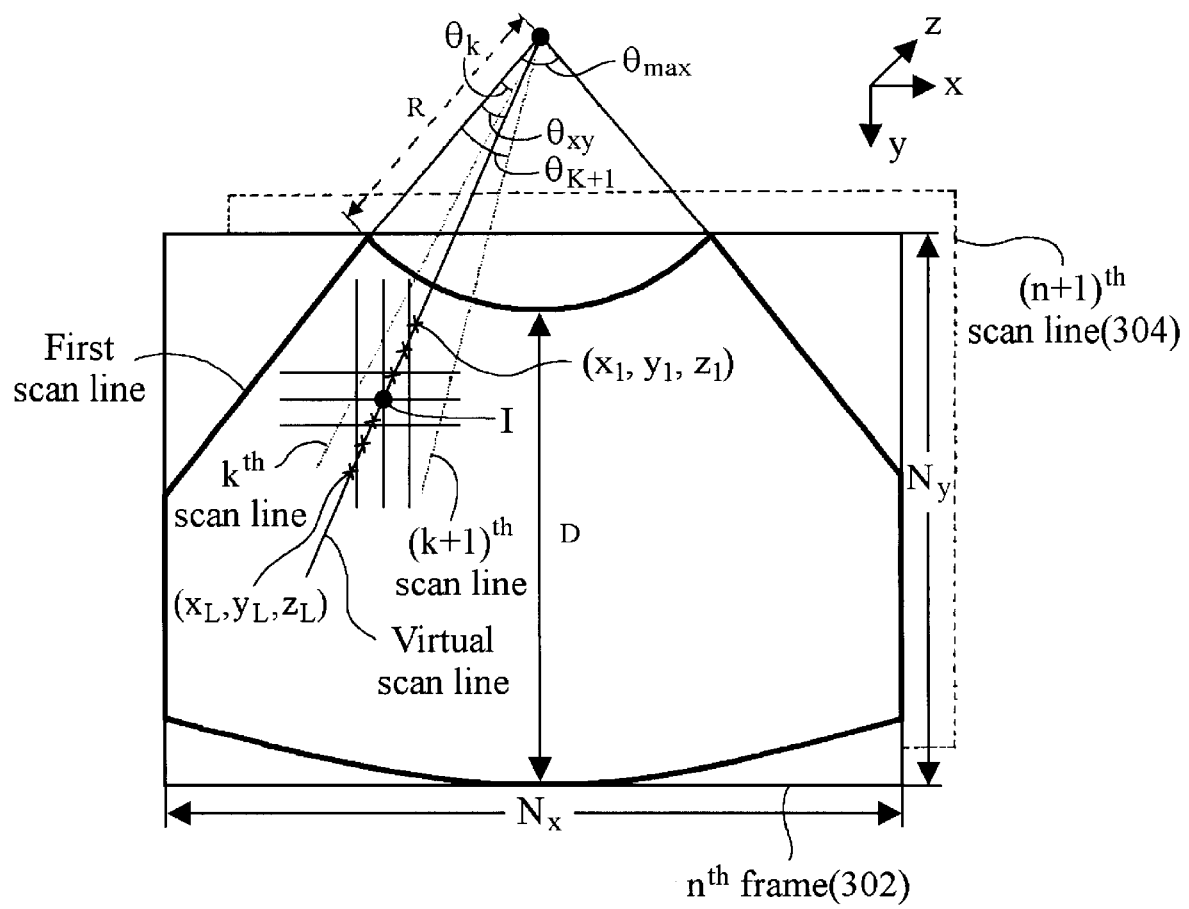
FIG. 3 is a diagram for explaining a method of acquisition of 3D data sets required to generate a 3D image.

FIG. 3 is a diagram of a method for performing receive-focusing on voxel I(x, y, z) in accordance with the present invention. In the following descriptions, M channels or transducers are used for transmission and reception for a predetermined scan line out of total of N scan lines within two consecutive frames.

For example, a curvilinear array of transducers (not shown) may be used wherein the radius of curvature of the array is R(mm) with scan angle $\theta_{max}$ and depth D(mm). To obtain 3D data sets with respect to a corresponding voxel, i.e., voxel I(x, y, z) of FIG. 2, determination of what data out of all RF data 202–208 is used is made by considering spatial distances between consecutive frames as well as between scan lines of each frame. The calculation of the time delay for the receive-focusing RF data 202–208 is also considered.

The data acquired by the curvilinear array (not shown) is converted to RF data as follows. After transmit-focusing ultrasound signals along one of N scan lines, which are radially spaced by angle $\Delta\theta$ with respect to apex $(X_A, Y_A, Z_A)$ of FIG. 3, an echo signal is sampled by M transducers at predetermined frequency $f_c$ and stored. Referring to FIG. 3, solid-line rectangle 302 represents the $n^{th}$ frame of two consecutive frames and dashed-line rectangle 304 represents the $(n+1)^{th}$ frame. Each of the two consecutive frames is $N_x \times N_y$.

Direct receive-focusing of the echo signal from voxel I(x, y, z) corresponding to a pixel on the display device by using RF data with respect to the most adjacent actual scan line, e.g., the $k^{th}$ scan line, within the $N^{th}$ frame occurs as follows. First, an actual scan line that is closest to a virtual scan line extending from apex $(X_A, Y_A, Z_A)$ to voxel I(x, y, z) that meets the following equation.

$$\text{Minimize} |\theta_{xy} - \theta_k|, 1 \leq k \leq N \qquad \text{Eq. (2)}$$

wherein $\theta_{xy}$ is the angle between the virtual scan line and a first actual scan line and $\theta_k$ is the angle between the first actual scan line and the $k^{th}$ actual scan line is identified. In order to directly obtain receive-focused data on voxel I(x, y, z), RF data that is received from transmit-focusing ultrasound signals on the $k^{th}$ actual scan line is used.

Figure 4:
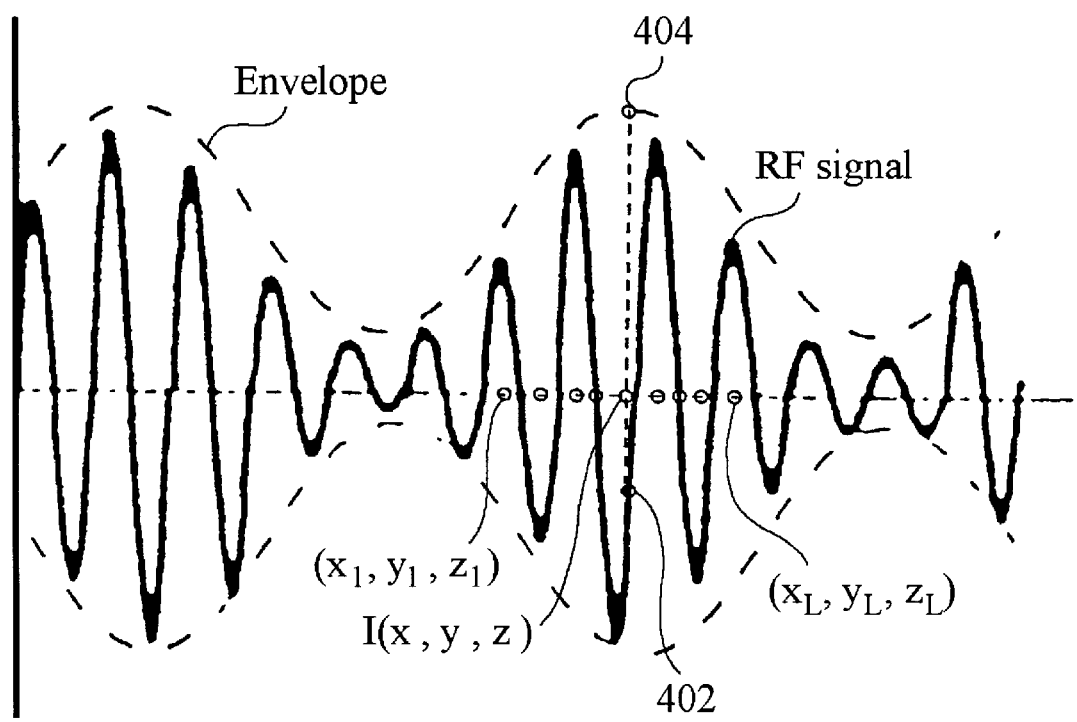
FIG. 4 is a comparison between RF signals receive-focused at voxels corresponding to pixels in the display device and values on the envelope.

For generating 3D data sets about voxel I(x, y, z), RF data that is receive-focused on L points including voxel I(x, y, z) on the virtual scan line is obtained, wherein the interval between each of L points is identical to a sampling rate and represented by an "X" on the virtual scan line. As is well known in the art, RF data about L points around voxel I(x, y, z) is needed because the receive-focused data of voxel I(x, y, z) will not be used directly to generate the 3D data sets for the pixels on the display device. Instead, the corresponding envelope of a waveform based on L points is used. Specifically, after obtaining receive-focused data about L points from point $(x_1, y_1, z_1)$ to point $(x_L, y_L, z_L)$ on the virtual scan line, a waveform representing the receive-focused data is made to generate 3D data sets for voxel I(x, y, z). A waveform represented by the receive-focused data is shown in FIG. 4. Referring to FIG. 4, though the signal detected at the voxel of interest is actually represented by small circle 402, the peak of the waveform, represented by a circle 404, is the effective data for the 3D data sets.

By repeating the process described above with reference to FIGS. 3 and 4 for all voxels within the object corresponding to the pixels on the display device, the 3D data sets required to display an entire 3D image can be obtained. Subsequently, 3D data sets corresponding to voxel I(x, y, z) are obtained through the above-mentioned process by using RF data with respect to an actual scan line, i.e., the $k^{th}$ scan line, of the $(n+1)^{th}$ frame most adjacent to voxel I(x, y, z).

Figure 5:
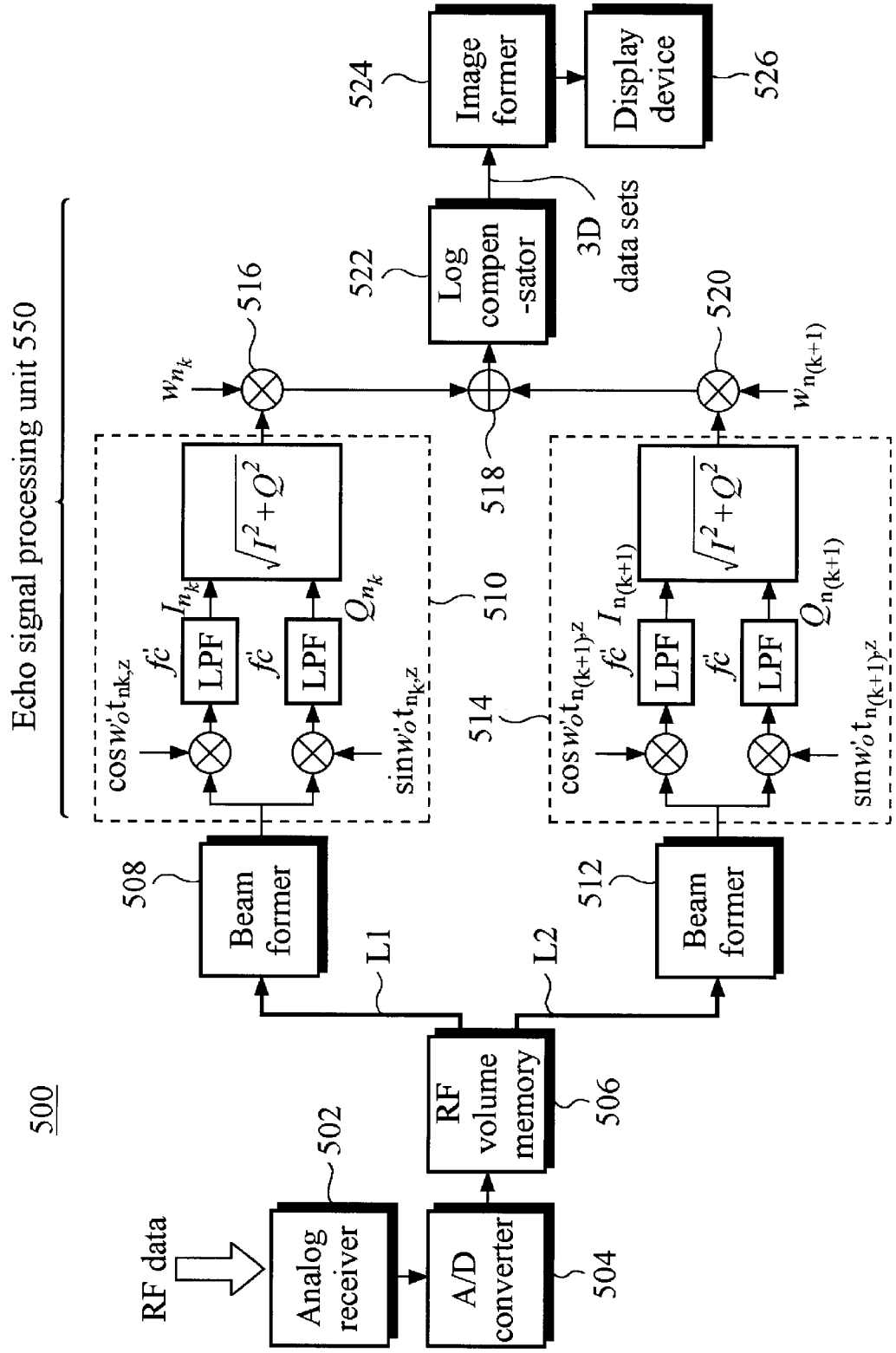
FIG. 5 is a schematic block diagram of a 3D ultrasound imaging system in accordance with an embodiment of the present invention.

Referring now to FIG. 5, a schematic block diagram of a 3D ultrasound imaging system in accordance with an embodiment of the present invention, 3D ultrasound imaging system 500 includes analog receiver 502, analog-to-digital (A/D) converter 504, RF volume memory 506, beam-formers 508 and 512, envelope detectors 510 and 514, log compensator 522, image former 524, and display device 526. System 500 does not include digital scan converter 110 of the conventional system 100.

Figure 1:
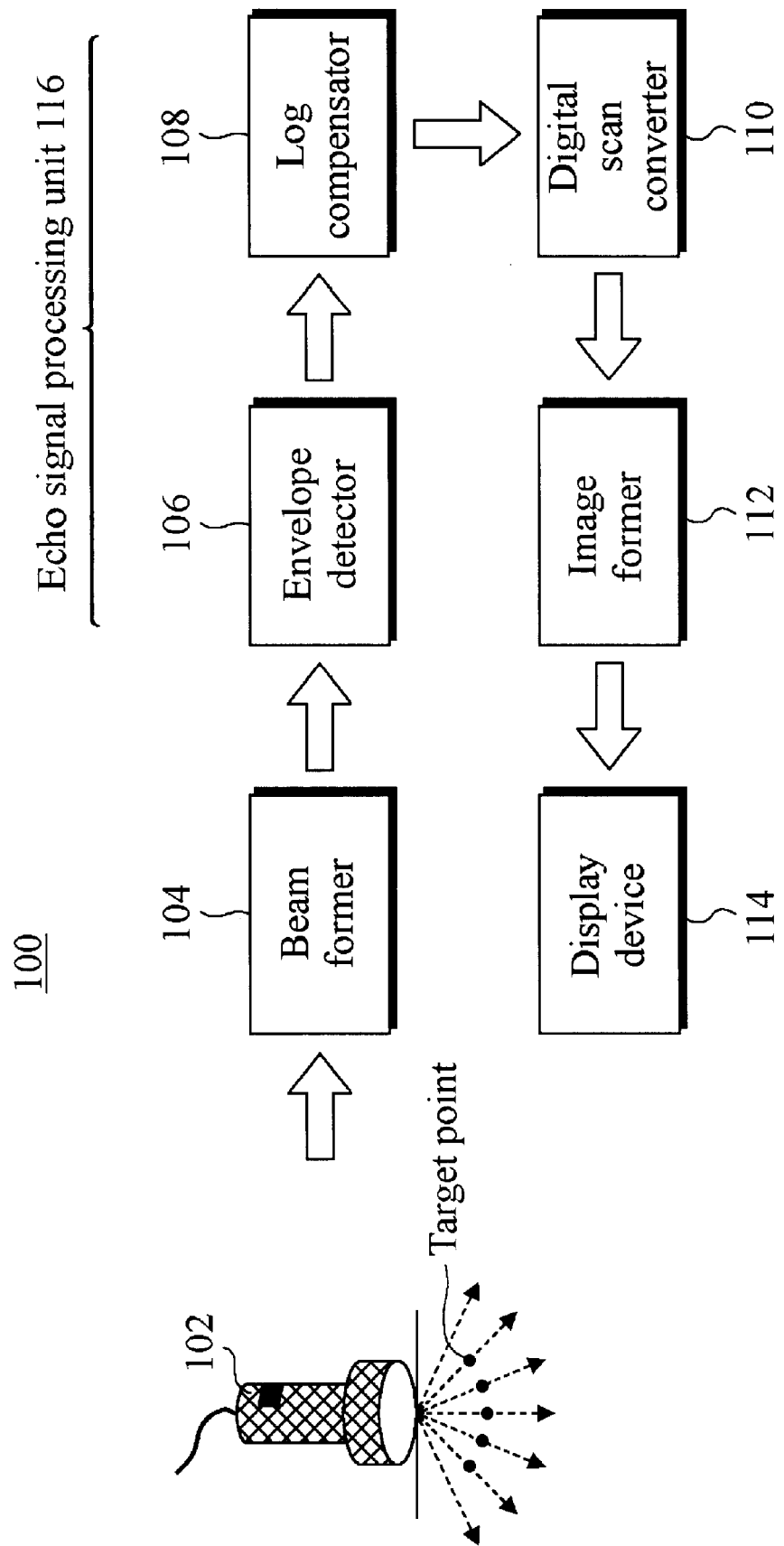
FIG. 1 is a schematic block diagram of a conventional three-dimensional (3D) ultrasound imaging system.

Analog receiver 502 receives RF data from an array of transducers (not shown), similar to array 102 in FIG. 1, and transfers them to A/D converter 504. A/D converter 504 converts the RF data sampled with a predetermined frequency, e.g., $f_s$, into digital RF data to transfer them to RF volume memory 506. RF volume memory 506 then stores the digital RF data. That is, RF volume memory 506 stores digital RF data with respect to each of the consecutive frames. The digital RF data stored in RF volume memory 506 are obtained by transmit-focusing ultrasound signals and sampling, with a predetermined frequency $f_s$, the RF signals received at M transducers about all N scan lines within each of P frames. The size of RF volume memory 506 required for storing digital RF data of one frame for a scan depth D is:

$$N \cdot M \cdot \frac{2D}{c} \cdot f_s \qquad \text{Eq. (3)}.$$

Thus, two times the RF volume memory given by Eq. 3 is required in the present invention, since at least two consecutive frames are used. The digital RF data stored in RF volume memory 506 is transferred through beamformers 508 and 512 to echo signal processing unit 550 including envelope detectors 510 and 514 and log compensator 522. Echo signal processing unit 550 generates 3D data sets corresponding to pixels on display device 526.

3D ultrasound imaging system 500 may be used to obtain 3D data sets with respect to voxel I(x, y, z) by using RF data 202 and 206 within the $n^{th}$ frame adjacent to voxel I(x, y, z). Specifically, 3D ultrasound imaging system 500 employs two beamformers 508 and 512 and is used in the case that voxel I(x, y, z) meets the following condition:

$$r_{n_k} \cdot r_{n_{(k+1)}} < r_{(n+1)_k} \cdot r_{(n+1)_{k-1}} \qquad \text{Eq. (4)}$$

wherein $r_{n_k}$ represents a distance between voxel I(x, y, z) and RF data 202 positioned on the $k^{th}$ scan line of the $n^{th}$ frame; $r_{(n+1)_k}$ is a distance between voxel I(x, y, z) and RF data 204 located on the $k^{th}$ scan line of the $(n+1)^{th}$ frame; $r_{n_{(k-1)}}$ represents a distance between voxel I(x, y, z) and RF data 206 positioned on the $(k+1)^{th}$ scan line of the $n^{th}$ frame; and $r_{(n+1)_{k+1}}$ is a distance between voxel I(x, y, z) and RF data 208 located on the $(k+1)^{th}$ scan line of the $(n+1)^{th}$ frame (as shown in FIG. 2). Here, n and k are integers. When voxel I(x, y, z) is adjacent to the $n^{th}$ frame of consecutive frames, system 500 performs the receive-focusing by using RF data 202 and 206 with respect to the most adjacent scan lines, i.e., the $k^{th}$ and $(k+1)^{th}$ scan lines. Thus, RF data 202 with respect to the $k^{th}$ scan line of the $n^{th}$ frame are transferred from RF volume memory 506 to beamformer 508 through line L1, while RF data 206 with respect to the $(k+1)^{th}$ scan line of the $n^{th}$ frame are transmitted through line L2.

Although, system 500 employs the quadrature demodulation technique for the envelope detection, the present invention is by no means limited thereto. Any suitable envelope detection method may be used.

Ultrasound signal does not attenuate uniformly, at all the frequencies, when propagating through a material. Higher frequency ultrasound signals attenuate much faster than lower frequency ultrasound signals. Therefore, the output signals from beamformers 508 and 512 should pass a dynamic band-pass filter, whose pass band varies depending on the distance traveled by a received ultrasound signal. Referring to FIG. 5, by changing frequency $\omega_0'$, of a sine or cosine signal that is multiplied to the outputs of beamformers 508 and 512 and cut-off frequency $f_c'$ of low-pass filter, dynamic band passing can be performed simultaneously in envelope detectors 510 and 512. Alternatively, a separate dynamic band-pass filter may be used.

Multiplier 516 multiplies weight $\omega_{n_k}$ to the output signal from envelope detector 510, which bears RF data 202 with respect to the $k^{th}$ scan line of the $n^{th}$ frame, and transfers it to adder 518. Similarly, multiplier 520 multiplies weight $w_{n_{(k+1)}}$ to the output signal from envelope detector 514, which bears RF data 206 with respect to the $(k+1)^{th}$ scan line of the $n^{th}$ frame, and transmits it to adder 518. Weights $\omega_{n_k}$ and $w_{n_{(k+1)}}$ are expressed as follows:

$$\omega_{n_k} = \frac{S_{k+1}}{(S_k + S_{k+1})} \qquad \text{Eq. (5)}.$$

$$\omega_{n_{k+1}} = \frac{S_k}{(S_k + S_{k+1})}$$

wherein $S_k$ represents a distance between voxel I(x, y, z) and the $k^{th}$ scan line; and $S_{k+1}$ is a distance between voxel I(x, y, z) and the $(k+1)^{th}$ scan line (as shown in FIG. 2).

Referring to FIG. 5, RF volume memory 506 is made up of a plurality of memory devices, each of which stores data for one image frame, in order to display the 3D image in real-time. Specifically, while RF data stored in one volume memory is used to display the 3D image, another volume memory should be able to store RF data for the next frame.

Adder 518 adds the weighted signals from multipliers 516 and 520 to transfer them to log compensator 522. Log compensator 522 compensates for the differences in the dynamic ranges of envelope detectors 510 and 514 and display device 526. Log compensated signals represent 3D data sets for use in the formation of the 3D image of the object. In order to display the 3D image, image former 524 is required to map the 3D data sets on the display device 526. Image former 524 maps the 3D data sets by using any of the known methods, such as surface rendering, volume rendering, and section reconstruction.

Figure 6:
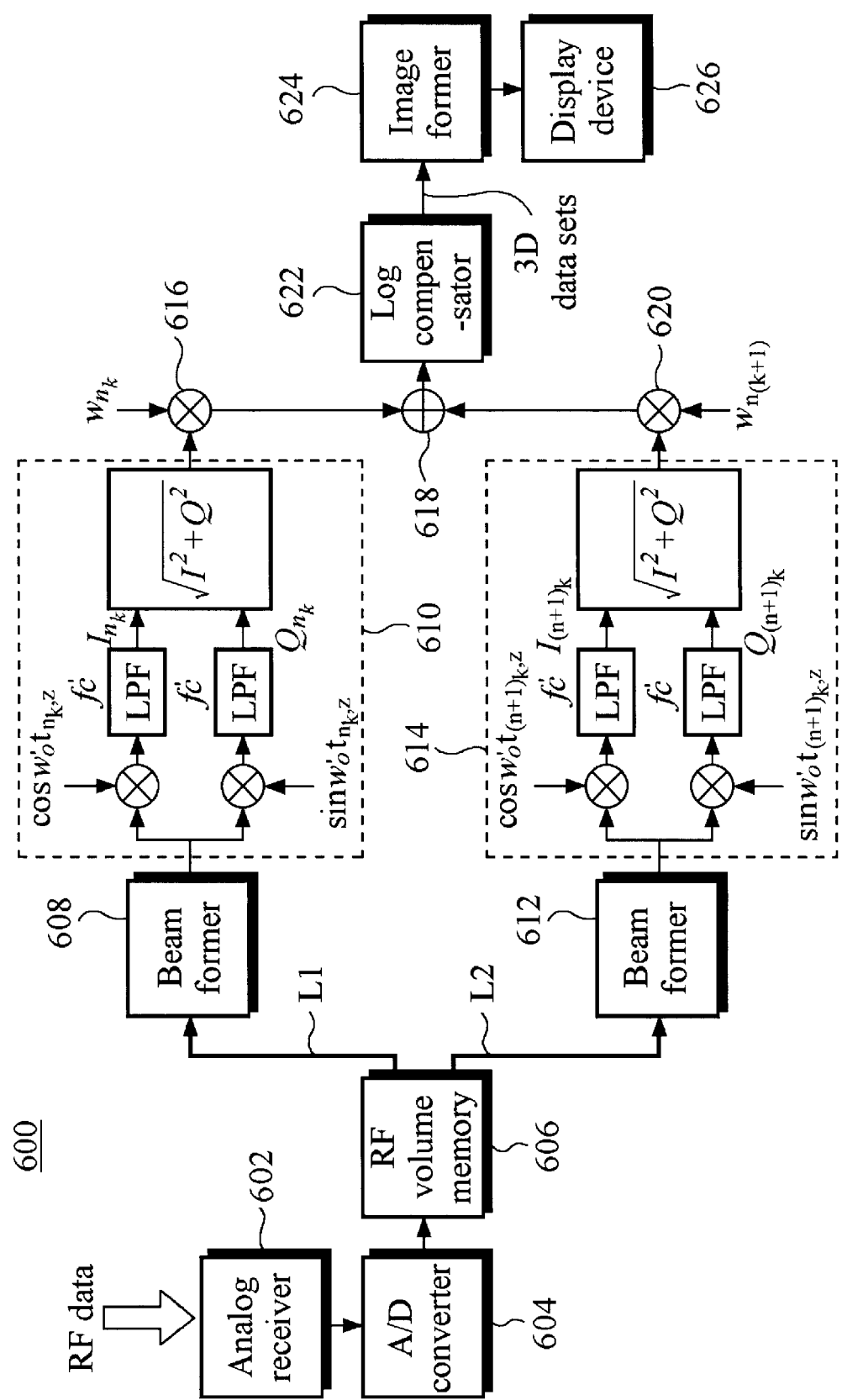
FIG. 6 is a schematic block diagram of a 3D ultrasound imaging system in accordance with another embodiment of the present invention.

Referring now to FIG. 6, a schematic block diagram of a 3D ultrasound imaging system in accordance with another embodiment of the present invention, 3D ultrasound imaging system 600 is used to obtain 3D data sets about voxel I(x, y, z) by using RF data 202 and 204 with respect to the $k^{th}$ scan line of the two consecutive frames, i.e., the $n^{th}$ and $(n+1)^{th}$ frames. Specifically, system 600 is used where voxel I(x, y, z) meets the following condition:

$$r_{n_k} \cdot r_{(n+1)_k} < r_{n_{(k+1)}} \cdot r_{(n+1)_{k+1}} \qquad \text{Eq. (6)}.$$

System 600 includes analog receiver 602, A/D converter 604, RF volume memory 606, two beamformers 608 and 612, two envelope detectors 610 and 614, two multipliers 616 and 620, log compensator 622, image former 624, and display device 626. The operation of system 600 is identical to that of the system 500 (shown in FIG. 5), except for the processing of signals in envelope detectors 610 and 614. Thus, only the operation of envelope detectors 610 and 614 will be described.

RF volume memory 606 provides RF data 202 with respect to the $k^{th}$ scan line of the $n^{th}$ frame via line L1 to envelope detector 610 through beamformer 608. Similarly, RF volume memory 606 transfers RF data 204 with respect to the $k^{th}$ scan line of the $(n+1)^{th}$ frame via line L2 to envelope detector 614 through beamformer 612.

Multiplier 616 multiplies weight $\omega_{n_k}$ to the output signal from envelope detector 610 to provide it to adder 618, while multiplier 620 multiplies weight $\omega_{(n+1)_k}$ to the output signal from envelope detector 614 to transfer it to adder 618. For this embodiment of the present invention, weights $\omega_{n_k}$ and $\omega_{(n+1)_k}$ are expressed as follows:

$$\omega_{n_k} = \frac{f_{n+1}}{(f_n + f_{n+1})} \qquad \text{Eq. (7)}.$$

$$\omega_{(n+1)_k} = \frac{f_n}{(f_n + f_{n+1})}$$

wherein $f_n$ represents a distance between voxel I(x, y, z) and the $n^{th}$ frame; and $f_{n+1}$ is a distance between voxel I(x, y, z) and the $(n+1)^{th}$ frame (as shown in FIG. 2).

Adder 618 adds the weighted signals from multipliers 616 and 620 to provide it to log compensator 622. Then, log compensator 622, image former 624, and display device 626 perform the same operation described above with reference to FIG. 5, thereby displaying the 3D image of the object.

Figure 7:
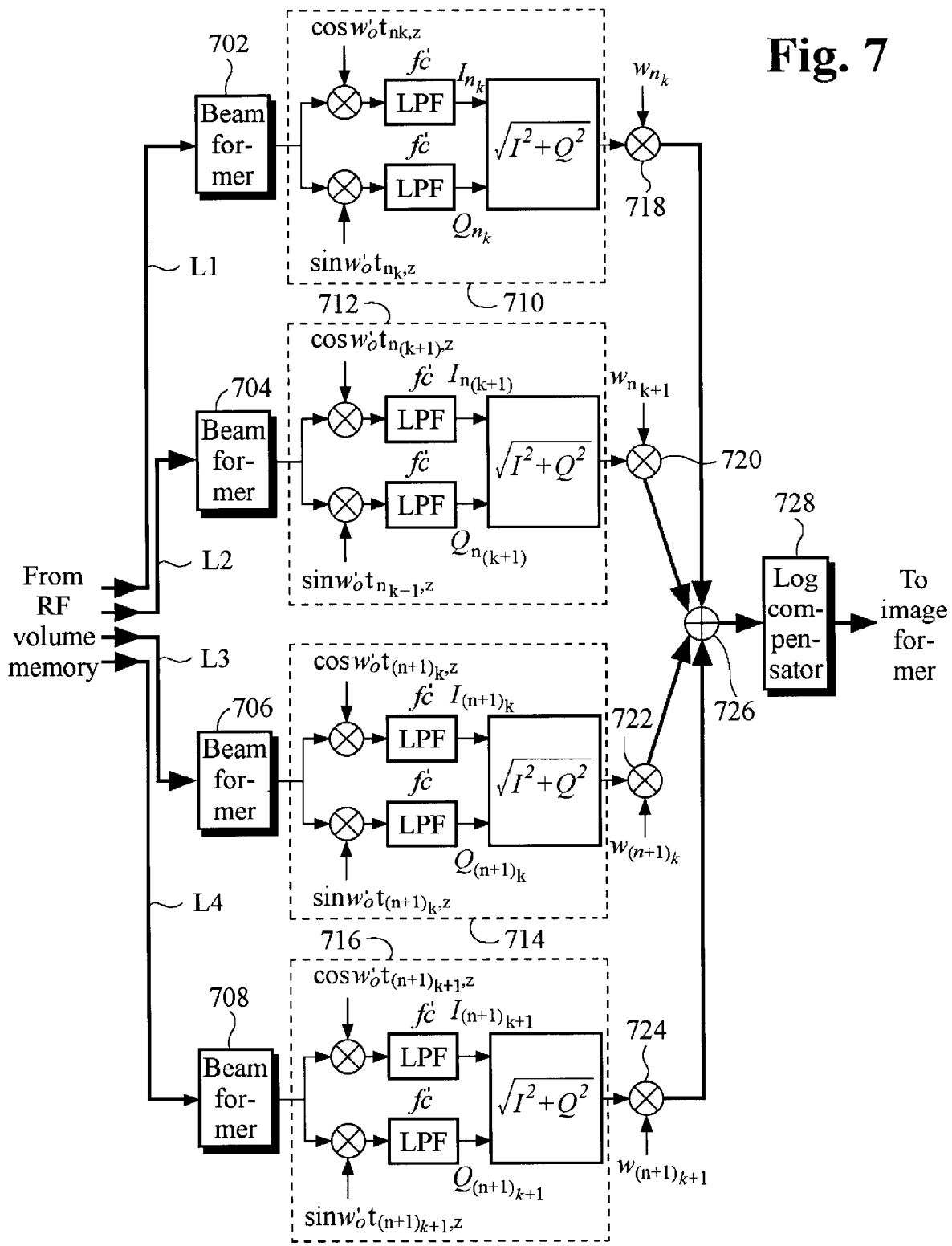
FIG. 7 is a schematic block diagram of a 3D ultrasound imaging system in accordance with yet another embodiment of the present invention.

Referring now to FIG. 7, a schematic block diagram of a 3D ultrasound imaging system in accordance with yet another embodiment of the present invention, four RF data surrounding voxel I(x, y, z) are used. Referring back to FIG. 2, they are marked with two dark-circles 202 and 204 and two hollow-triangles 206 and 208. 3D ultrasound imaging system 700 is identical to system 600, except for the operation of beamformers 702, 704, 706, and 708, envelope detectors 710, 712, 714, and 716, multipliers 718, 720, 722, and 724, and adder 726. Only the different operations will be described.

An RF volume memory (not shown) provides beamformers 702, 704, 706, and 708 with four RF data 202, 204, 206, and 208 with respect to consecutive frames adjacent to voxel I(x, y, z). Specifically, RF data 202 with respect to the $k^{th}$ scan line of the $n^{th}$ frame is provided to envelope detector 710 through beamformer 702; RF data 206 with respect to the $(k+1)^{th}$ scan line of the $n^{th}$ frame is transferred to envelope detector 712 through beamformer 704; RF data 204 with respect to the $k^{th}$ scan line of the $(n+1)^{th}$ frame is provided to envelope detector 714 through beamformer 706; and RF data 208 with respect to the $(k+1)^{th}$ scan line of the $(n+1)^{th}$ scan line is transferred to envelope detector 716 through beamformer 708.

After completing the envelope detection, multiplier 718 multiplies weight $\omega_{n_k}$ to the output signal from envelope detector 710; multiplier 720 multiplies weight $\omega_{n_{k+1}}$ to the output signal from envelope detector 712; multiplier 722 multiplies weight $\omega_{(n+1)_k}$ to the output of envelope detector 714; and multiplier 724 multiplies weight $\omega_{(n+1)_{k+1}}$ to the output of envelope detector 716.

In this embodiment of the present invention, weights $\omega_{n_k}$, $\omega_{n_{k+1}}$, $\omega_{(n+1)_k}$, $\omega_{(n+1)_{k+1}}$ are expressed as follows:

$$\omega_{n_k} = \frac{f_{n+1}}{(f_n + f_{n+1})} \times \frac{S_{k+1}}{(S_k + S_{k+1})}$$

$$\omega_{n_{k+1}} = \frac{f_{n+1}}{(f_n + f_{n+1})} \times \frac{S_k}{(S_k + S_{k+1})}$$

$$\omega_{(n+1)_k} = \frac{f_n}{(f_n + f_{n+1})} \times \frac{S_{k+1}}{(S_k + S_{k+1})}$$

$$\omega_{(n+1)_{k+1}} = \frac{f_n}{(f_n + f_{n+1})} \times \frac{S_k}{(S_k + S_{k+1})}$$

Eq. (8).

The weighted signals are provided to log compensator 728. Log compensator 728 then compensates for the differences of the weighted signals in the dynamic ranges of envelope detectors 710, 712, 714, and 716 and the display device (not shown) to generate 3D data sets of the 3D image.

System 700 employs four beamformers 702, 704, 706, and 708 and does not require a specific condition with respect to voxel I(x, y, z), i.e., the relationship among the distances of voxel I(x, y, z) and four RF data 202, 204, 206, and 208.

A person skilled in the art will appreciate that the number of beamformers and envelope detectors varies depending on the number of RF data to be used for direct receive-focusing of echo signals.

By directly receive-focusing echo signals of the voxel within the scan region of the object corresponding to a pixel of the display device, the present invention does not require the digital scan conversion used in the prior art. Therefore, the present invention avoids distortion of the 3D image due to digital scan conversion and provides an improved 3D image.

The present invention is also more effective for implementing "zoom" functions, wherein in case that the number of scan lines available for generating the zoomed image decreases or the distance between scan lines is increased due to a broader scan angle.

Furthermore the present invention dramatically improves the quality of a 3D image for cases in which the number of pixels on the display device is increased, by directly receive-focusing echo signals from voxels corresponding to all the pixels after receive-focusing the echo signals from target points on the actual scan lines, without calculating 3D data sets of the voxel corresponding to a pixel on the display device through digital scan conversion.

While the present invention has been shown and described with respect to particular embodiments, it will be apparent to those skilled in the art that many changes and modifications may be made without departing from the spirit and scope of the invention as defined in the appended claims.

What is claimed is:

1. A three-dimensional (3D) ultrasound imaging system for forming a 3D image, comprising:

a display device;

one or more transducers, for transmitting ultrasound signals toward an object and receiving echo signals from target points surrounding a voxel corresponding to a pixel on the display device, wherein the voxel is on a scanning region of the object and the target points are on scan lines of two consecutive frames adjacent to the voxel within the scanning region;

signal storing means for storing the echo signals from the one or more transducers;

signal processing means for processing the echo signals stored in the signal storing means to obtain 3D data sets of the voxel; and image forming means for forming a 3D image based on the 3D data sets, wherein, at the signal processing means, the 3D data sets are obtained by determining weights for each of the echo signals based on distances between the voxel and the target points, and weighting the echo signals data with the determined weights, and wherein the weights are determined as follows:

$$\omega_{n_k} = \frac{f_{n+1}}{(f_n + f_{n+1})} \times \frac{S_{k+1}}{(S_k + S_{k+1})}$$

$$\omega_{n_{k+1}} = \frac{f_{n+1}}{(f_n + f_{n+1})} \times \frac{S_k}{(S_k + S_{k+1})}$$

$$\omega_{(n+1)_k} = \frac{f_n}{(f_n + f_{n+1})} \times \frac{S_{k+1}}{(S_k + S_{k+1})}$$

$$\omega_{(n+1)_{k+1}} = \frac{f_n}{(f_n + f_{n+1})} \times \frac{S_k}{(S_k + S_{k+1})}$$

wherein $\omega_{n_k}$ is a weight with respect to a target point on a $k^{th}$ scan line among the scan lines in a $n^{th}$ frame of the two consecutive frames; $\omega_{n_{k+1}}$ is a weight with respect to a target point on a $(k+1)^{th}$ scan line among the scan lines in the $n^{th}$ frame; $\omega_{(n+1)_k}$ is a weight with respect to a target point on the $k^{th}$ scan line in a $(n+1)^{th}$ frame of the two consecutive frames; $\omega_{(n+1)_{k+1}}$ is a weight with respect to a target point on the $(k+1)^{th}$ scan line in the $(n+1)^{th}$ frame; $f_n$ represents a distance between the voxel and the $n^{th}$ frame; $f_{n+1}$ represents a distance between the voxel and the $(n+1)^{th}$ frame; $S_k$ represents a distance between the voxel and the $k^{th}$ scan line; and $S_{k+1}$ represents a distance between the voxel and the $(k+1)^{th}$ scan line.

2. The system of claim 1, wherein the one or transducers transmit and focus the ultrasound signals to the target points and receive the echo signals reflected from the target points.

3. The system of claim 1, wherein the echo signals are stored in the signal storing means in the form of Radio Frequency (RF) data.

4. The system of claim 3, wherein the signal storing means further comprises:
an RF volume memory, wherein the RF volume memory stores RF data with respect to the two consecutive frames.

5. The system of claim 1, wherein the 3D image forming means further forms the 3D image through at least one of surface rendering, volume rendering, and section reconstruction based on the 3D data sets.

6. The system of claim 1, wherein the signal processing means further detects an envelope of the received echo signals to obtain the 3D data sets.

* * * * *